US011452456B2

(12) United States Patent
Kirenko et al.

(10) Patent No.: US 11,452,456 B2
(45) Date of Patent: Sep. 27, 2022

(54) DEVICE, SYSTEM AND METHOD FOR DETERMINING THE CORE BODY TEMPERATURE OF A SUBJECT

(71) Applicant: KONINKLIJKE PHILIPS N.V., Eindhoven (NL)

(72) Inventors: Ihor Olehovych Kirenko, Veldhoven (NL); Caifeng Shan, Veldhoven (NL); Ronaldus Maria Aarts, Geldeop (NL)

(73) Assignee: Koninklijke Philips N.V., Eindhoven (NL)

( * ) Notice: Subject to any disclaimer, the term of this patent is extended or adjusted under 35 U.S.C. 154(b) by 538 days.

(21) Appl. No.: 16/340,713

(22) PCT Filed: Oct. 26, 2017

(86) PCT No.: PCT/EP2017/077379
§ 371 (c)(1),
(2) Date: Apr. 10, 2019

(87) PCT Pub. No.: WO2018/082991
PCT Pub. Date: May 11, 2018

(65) Prior Publication Data
US 2019/0313914 A1     Oct. 17, 2019

(30) Foreign Application Priority Data

Nov. 1, 2016 (EP) .................................. 16196692

(51) Int. Cl.
*A61B 5/01* (2006.01)
*A61B 5/00* (2006.01)
(52) U.S. Cl.
CPC ............ *A61B 5/015* (2013.01); *A61B 5/0075* (2013.01); *A61B 5/0077* (2013.01); *A61B 2562/0271* (2013.01); *A61B 2576/02* (2013.01)

(58) Field of Classification Search
USPC ........................................................ 600/549
See application file for complete search history.

(56) References Cited

U.S. PATENT DOCUMENTS 9,501,704 B2    11/2016   Matsuo
2004/0254472 A1*  12/2004   McQuilkin ............ A61B 5/015
600/549

(Continued)

FOREIGN PATENT DOCUMENTS

DE      102004027443         7/2005
WO      2011/151806 A1      12/2011

OTHER PUBLICATIONS

Blanik et al: "Hybrid optical imaging technology for long-term remote monitoring of skin perfusion and temperature behavior", J. Biomed. Opt. 19(1), 016012 (Jan. 17, 2014).

(Continued)

*Primary Examiner* — Fabricio R Murillo Garcia

(57) ABSTRACT

The present invention relates to a device, system and method for determining the core body temperature of a subject. To enable continuous core body determination without having to place or direct a sensor at a precise position of the subject's body, the device comprises an image data input (31) for obtaining image data (11) of a subject's skin, a thermal sensor data input (32) for obtaining thermal sensor data (21) of the subject's skin, an image analysis unit (33) for deriving photoplethysmography, PPG, signals from the obtained image data and for detecting one or more skin areas (34) having the strongest PPG signals, and a temperature determination unit (35) for determining the core body temperature (36) of the subject from obtained thermal sensor data for the detected one or more skin areas.

18 Claims, 2 Drawing Sheets

(56) References Cited

U.S. PATENT DOCUMENTS

| | | | | |
|---|---|---|---|---|
| 2007/0153871 | A1 | 7/2007 | Fraden | |
| 2013/0215928 | A1* | 8/2013 | Bellifemine | A61B 5/01 374/121 |
| 2014/0275832 | A1 | 9/2014 | Muehlsteff | |
| 2015/0051521 | A1 | 2/2015 | Woerlee | |
| 2015/0379370 | A1* | 12/2015 | Clifton | A61B 5/0075 382/128 |
| 2016/0027171 | A1* | 1/2016 | Spahn | A61B 5/015 382/128 |
| 2016/0206216 | A1 | 7/2016 | Kirenko | |
| 2020/0345302 | A1* | 11/2020 | Bly | A61B 5/02055 |

OTHER PUBLICATIONS

Verkruysse et al: "Remote plethysmographic imaging using ambient light", Optics Express, 16(26), Dec. 22, 2008, pp. 21434-21445.

Tiger Medical, ARC InstaTemp non-touch thermometer. https://www.tigermedical.com/Departments/Brands-Categories/ARC-Devices.aspx.

Exergen Corporation, Temporal Artery Thermometer, http://www.exergen.com/medical/TAT/2000c.htm.

Allegaert et al: "Tympanic, infrared skin, and Temproal Artery Scan Thermometers compared with Rectal Measurement in Children: a real-life Assessment", Current Therapeutic Research, Esevier, vol. 76, Dec. 2014, pp. 34-38.

Blanik et al: "Detection and Analysis of Temperature-sensitive Dermal Blood Perfusion Dynamics and Distribution by a Hybrid Camera System", IEEE, 2015, pp. 2383-2386.

"Blood Pulsating Imaging" Thesis, University of Eastern Finland, Dec. 19, 2014.

PCT International Search Report and Written Opinion, dated Feb. 19, 2018, for International application No. PCT/EP2017/077379 filed Oct. 26, 2017.

* cited by examiner

DEVICE, SYSTEM AND METHOD FOR DETERMINING THE CORE BODY TEMPERATURE OF A SUBJECT

CROSS REFERENCE TO RELATED APPLICATIONS

This application is the U.S. National Phase application under 35 U.S.C. § 371 of International Application No. PCT/EP2017/077379 filed Oct. 26, 2017, published as WO 2018/082991 on May 11, 2018, which claims the benefit of European Patent Application Number 16196692.4 filed Nov. 1, 2016. These applications are hereby incorporated by reference herein.

FIELD OF THE INVENTION

The present invention relates to a device, system and method for determining the core body temperature of a subject, such as a person or animal.

BACKGROUND OF THE INVENTION

The best place to measure core temperature is the center of the heart, but this can be done only under a doctor's supervision. Doctors know that measurement of the blood temperature in a major artery accurately reflects true body temperature. Several methods have been developed to measure core body temperature from skin surface using so-called Temporal Artery Scan (TAS) approach. It has been shown that this approach provides measurement closest to rectal measurements. The temporal artery is connected to the heart via the carotid artery, directly leading from the aorta, which is the main trunk of the arterial system. It offers constant blood flow. It is the only such artery that is positioned close enough to the skin surface to provide access needed to take an accurate measurement. It is easy to use because it is ideally located at the front portion of the forehead.

Several devices have been introduced to the market, aiming at unobtrusive core temperature measurement using the TAS approach. However, the accuracy of such devices depends on the accuracy of spatial placement of the sensor. Hence, they are generally not suitable for continuous use, because the temperature sensing should be performed continuously over the measurement region. Moreover, such devices may fail if the skin is moist, for example by sweating. In this case the result is much too low core body temperatures.

Therefore, several new methods have been proposed recently, which make use of an array of IR sensors to scan a part of a skin and automatically detect the "hottest" spot within the area, which would correspond to a location above an artery. Corresponding devices introduced recently to the market are able to measure core body temperature accurately without contact with a skin. However, although such devices provide for unobtrusive core body measurement, they are not suitable for continuous remote monitoring (e.g. in NICU incubator), since the device should be manually pointed towards a certain part of a body (e.g. the forehead).

Furthermore, known devices rely on the assumption that a local spot of the skin with highest surface temperature corresponds to a location on top of an artery, which might not be always true, e.g. due to local skin irritation, proximity to an ambient heat sources, etc.

BLANIK NIKOLAI ET AL: "Hybrid optical imaging technology for long-term remote monitoring of skin perfusion and temperature behavior", J. Biomed. Opt. 19(1), 016012 (Jan. 17, 2014). doi:10.1117/1.JBO.19.1.016012 discloses a combined hybrid application using photoplethysmography imaging (PPGI) and infrared thermography imaging (IRTI), which supplement each other for monitoring a wide range of basic vital parameters. PPGI enhances the classical contact-based photoplethysmography. Approved evaluation algorithms of the well-established PPG method can easily be adapted for detection of heart rate, heart rate variability, respiration rate (RR), respiratory variability (RV), and vasomotional activity with PPGI. The IRTI method primarily records temperature distribution of the observed object, but information on RR and RV can also be derived from IRTI by analyzing the development of temperature distribution in the nasal region. The main advantages of both monitoring methods are unobtrusive data acquisition and the possibility of assessing spatial assignment between vital parameters and body region. Hence, these methods enable long-term monitoring or the monitoring of effects with special local characteristics.

Hence, there is still a need for a solution that overcomes these disadvantages of known temperature measurement methods, namely the requirement to point the device towards a part of a skin around an artery (e.g. the forehead), thus enabling continuous automated core body temperature measurement, and/or that they rely on a measurement of a particular local spot of the skin.

SUMMARY OF THE INVENTION

It is an object of the present invention to provide a device, system and method that enable accurately and reliably determining the core body temperature of a subject continuously without having to point the device to a particular part of the skin.

In a first aspect of the present invention a device for determining the core body temperature of a subject is presented comprising
- an image data input for obtaining image data of a subject's skin,
- a thermal sensor data input for obtaining thermal sensor data of the subject's skin,
- an image analysis unit for deriving photoplethysmography, PPG, signals from the obtained image data and for detecting one or more skin areas having the strongest PPG signals, and
- a temperature determination unit for determining the core body temperature of the subject from obtained thermal sensor data for the detected one or more skin areas.

In a still further aspect of the present invention a system for determining the core body temperature of a subject is presented comprising
- an imaging unit for acquiring image data of a subject's skin,
- a thermal sensor for acquiring thermal sensor data of the subject's skin, and
- a device as disclosed herein for determining the core body temperature of a subject.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to make use of PPG imaging to detect skin areas (i.e. groups of one or more pixels) with the strongest PPG signals. Hence, the present invention makes use of the Temporal Artery Scan approach, but provides an automated localisation of a skin area around an artery using the PPG imaging approach.

PPG imaging is generally known and e.g. described in many patent documents and papers. Plethysmography generally refers to the measurement of volume changes of an organ or a body part and in particular to the detection of volume changes due to a cardio-vascular pulse wave traveling through the body of a subject with every heartbeat. Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

This technique is evaluated in contact PPG devices (e.g. pulse oximeters) for contact measurements and non-contact, remote PPG (rPPG) devices for unobtrusive measurements. For instance, Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

The proposed approach has the advantage that two different modalities are used for detection of the region of interest (ROI) around the skin area with the artery, and for measuring a skin temperature within that ROI. Thus, a higher robustness to any influence of ambient temperature and other sources of changes of a skin surface temperature is achieved. Further, making use of PPG imaging for automated detection of the ROI around an artery enables continuous automated monitoring of the core body temperature without the need to manually point a sensor (e.g. an IR sensor) towards a certain body part. The proposed combination of PPG imaging with ROI spatial tracking thus enables continuous core body temperature measurement even during motion of the subject.

There are various preferred embodiments to find a skin area with the strongest PPG signal. In an embodiment said image analysis unit is configured to detect one or more skin areas having the strongest PPG signals by detecting, based on said PPG signals, one or more skin areas having the highest blood pulsatility. In another embodiment said image analysis unit is configured to detect one or more skin areas having the strongest PPG signals by detecting one or more skin areas having PPG signals with the highest intensity in a predetermined frequency range, in particular the typical frequency range of the subject's pulse rate.

Said temperature determination unit may be configured to determine the core body temperature of the subject from the acquired thermal sensor data separately for two or more detected skin areas and to combine the determined core body temperature values determined for the two or more detected skin areas. This further increases the accuracy of the temperature determination.

In an embodiment said temperature determination unit is configured to determine the core body temperature of the subject by analyzing the difference between the temperature of the skin area showing the strongest PPG signal and the temperature of other skin areas. This provides a simple but accurate way of determining the core body temperature.

In an embodiment said image analysis unit is configured to track one or more detected skin areas over time. This is particularly preferred if the subject is moving.

Further, in an embodiment the image analysis unit may be configured to identify anatomical regions and/or the geometrical structure of the subject within the obtained image data, and the temperature determination unit may be configured to adapt the determination of the core body temperature according to the identified anatomical region and/or the identified geometrical structure of the subject. For instance, dedicated calibration parameters may be used for an area around a particular body area such as the forehead. This further improves the accuracy of the temperature determination.

The proposed system comprises an imaging unit, a thermal sensor and a device disclosed herein and as briefly described above. The thermal sensor may comprise a longwave camera unit for acquiring thermal images in the longwave infrared spectrum. The imaging unit may comprise an imaging unit, such as a camera, for acquiring images in the visible and/or infrared light spectrum.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
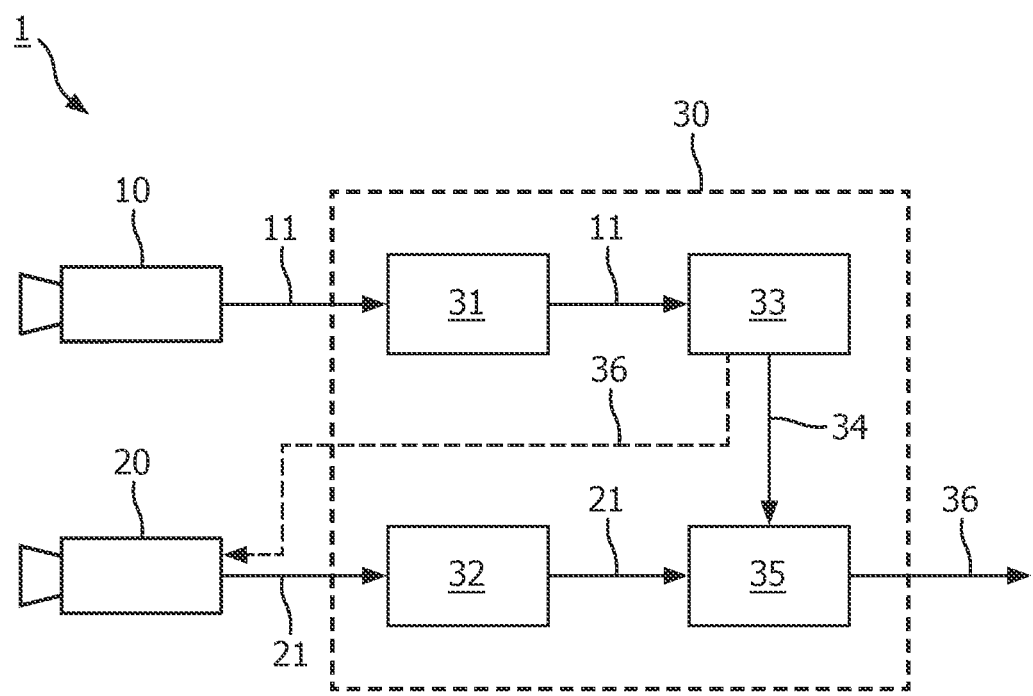
FIG. 1 shows a schematic diagram of an embodiment of a system and a device according to the present invention.

FIG. 1 shows a schematic diagram of an embodiment of a system 1 and a device 30 for determining the core body temperature of a subject according to the present invention. The system 1 comprises an imaging unit 10 for acquiring image data 11 of a subject's skin, for instance a camera for taking a time series of images or video data of the subject's forehead. The system 1 further comprises a thermal sensor 20 for acquiring thermal sensor data 21 of the subject's skin, e.g. an infrared camera for taking a time series of infrared images or infrared video data of the subject's forehead. The imaging unit 10 and the thermal sensor 20 may be configured as separate devices or may be integrated into a common device, e.g. a camera device. Further, they are configured (e.g. controlled or synchronized) to acquire the image data and the thermal sensor data simultaneously.

The system 1 further comprises the device 30 for determining the core body temperature of a subject. The device 30 may be implemented in soft- and/or hardware, e.g. as a dedicated device, or a processor or computer that is programmed accordingly. The device 30 may be arranged separate from the imaging unit 10 and the thermal sensor 20 and connected to them wirelessly or in a wired manner, but may alternatively be integrated with them in the same common device, e.g. a common camera device or a user device, such as a smartphone, which is provided with corresponding hardware and software.

The device 30 comprises an image data input 31 for obtaining the image data 11 of the subject's skin acquired by the imaging unit 10 and a thermal sensor data input 32 for obtaining the thermal sensor data 21 of the subject's skin acquired by the thermal sensor 20. An image analysis unit 33 is provided for deriving PPG signals from the obtained image data 11 and for detecting one or more skin areas 34 having the strongest PPG signals. A temperature determination unit 35 determines the core body temperature 36 of the subject from the obtained thermal sensor data 21 for the detected one or more skin areas 34.

An embodiment of the present invention makes use of the same physiological principle as used in TAS sensors—estimation of core temperature by measuring a surface (skin) temperature above temporal artery. The major fundamental difference is in the method of automated selection of skin area on top of the artery. In TAS sensors, it is assumed that the hottest skin area at a certain body location (e.g. forehead) corresponds to the location of the artery. According to the present invention this location is detected as the areas with strongest PPG amplitude. Such an approach is more robust to influences of ambient temperature and resolution of IR sensor and should be more accurate and reliable.

According to a preferred embodiment of the system 1 two types of camera sensors are used that are spatially aligned: an RGB or near-infrared (nIR) camera (as imaging unit 10; also called PPG imaging camera) to measure blood pulsatility in a large skin area, and a thermal 2D sensor or IR sensor (as thermal sensor 20) to measure the surface temperature within a region of interest (ROI) detected by the imaging unit.

With this embodiment, in a first step the RGB or nIR camera (i.e. the imaging unit 10) acquires image data from which PPG signals are extracted per a spatial location (one pixel, or a group of pixels), thus forming a 2D PPG image. Within the extracted PPG imaging area, one or more ROIs around locations with large amplitudes of PPG signals are automatically selected. The size of the selected ROI should be large enough to cover areas with high blood pulsatility, and areas with small pulsatility.

Figure 2:
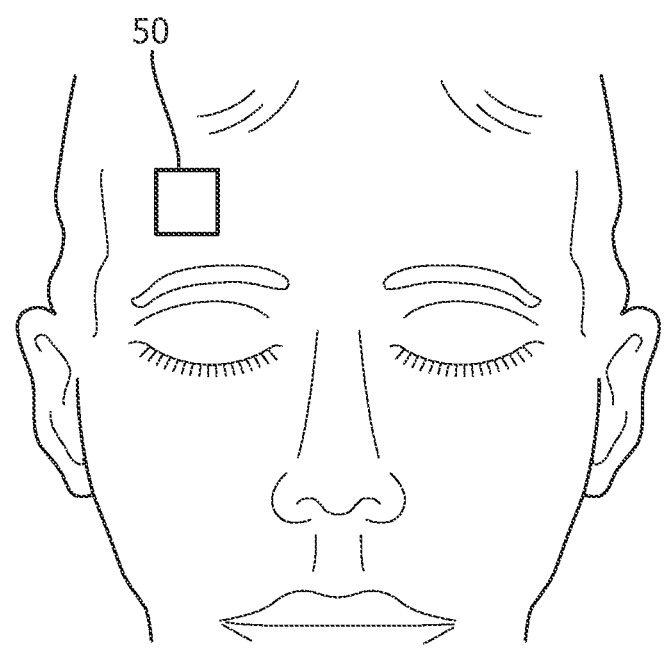
FIG. 2 shows an exemplary image of a subject's face.
Figure 3:
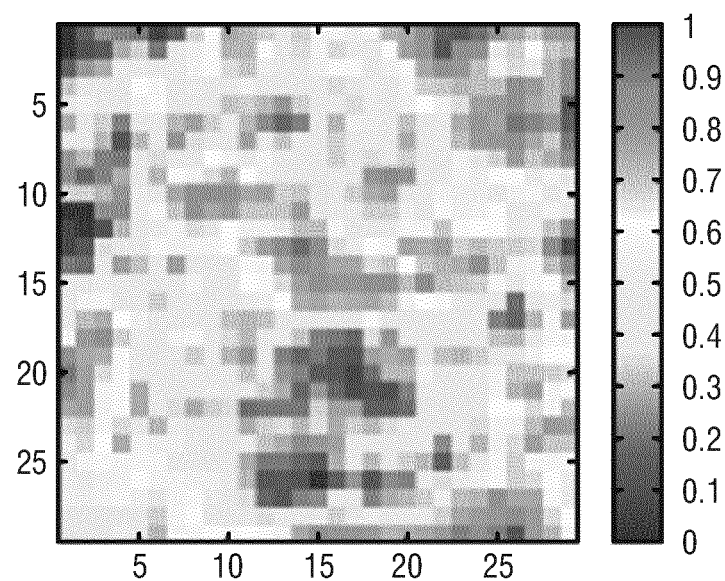
FIG. 3 shows a 2D map of the PPG amplitudes of the PPG image shown in FIG. 2.
Figure 4:
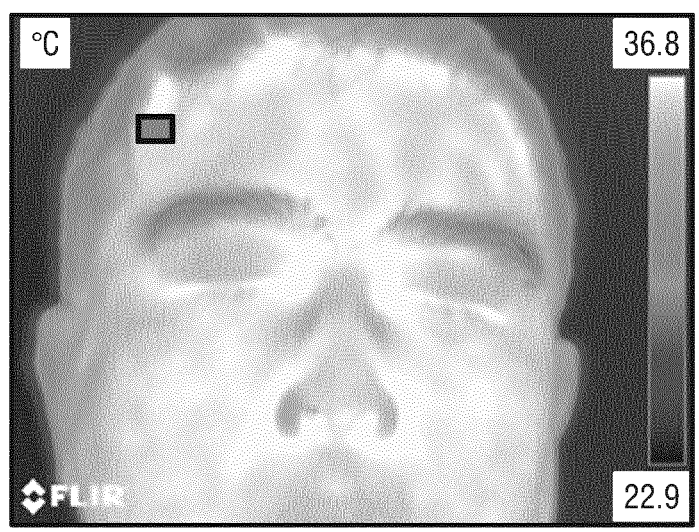
FIG. 4 shows an exemplary thermal image of a subject's face.

An illustration of 2D PPG imaging on the forehead is shown in FIG. 2 and FIG. 4. FIG. 2 depicts an exemplary image of a subject's face and FIG. 3 shows a 2D map of the PPG amplitudes of a selected part 50 in the image shown in FIG. 2. For the skin area in the rectangle 50 in FIG. 2, the PPG signals may be extracted at every spatial location. The 2D map of the amplitude of the PPG signals, shown in FIG. 3, shows the blood pulsatility of this skin area.

Instead of using the blood pulsatility of the skin area for selecting one or more ROI(s) with strongest PPG signals, one or more skin areas having PPG signals with the highest intensity in a predetermined frequency range (e.g. the typical frequency range of heart beat) may be used. For instance, a FFT of the PPG signals may be made to analyze the spectrum of the PPG signals for selecting those ROI(s).

The one or more ROI(s) selected from the PPG image is (are) then analyzed to extract the core body temperature.

In a second step, with this embodiment the thermal camera (i.e. the thermal sensor 20), spatially aligned with the imaging unit 10, registers at least one ROI selected in the previous step based on the PPG imaging. Hence, in this embodiment the thermal sensor 20 does not need to acquire thermal sensor data 21 from the whole skin area that is imaged by the imaging unit 10, but only from one or more selected ROIs of the skin area. Thus, in this preferred embodiment there may be a control signal 36 back from the device 30, in particular the image analysis unit 33, to the thermal sensor 20 to indicate the selected ROIs to the thermal sensor 20 for enabling it to acquire the thermal sensor data 21 from the selected ROIs. This control signal 36 is indicated as dashed line in FIG. 1.

In a third step, with this embodiment for each of the selected ROIs within a thermal image, an approach is applied to select a skin area for temperature measurement based on the same physiological effect exploited in TAS approach, but the spatial "hottest" area is selected as an area with the locally largest PPG amplitude. This approach is applied to extract a core body temperature by analyzing the difference between the measured temperature at the "hottest" skin spot (i.e. a location around a PPG signal with largest amplitude) and other parts of the ROI. FIG. 4 illustrates an example by showing an exemplary thermal image of a subject's face.

In another embodiment, several ROIs are segmented within the image data and analyzed in parallel. Further, a combined analysis is applied to the output of the segmentation and the first parallel analysis to improve the accuracy and robustness of temperature measurement.

In yet another embodiment, ROI tracking is applied to ROIs segmented within the image data. This enables a monitoring of core body temperature even during body motion.

In still a further embodiment, PPG imaging is combined with anatomical skin segmentation (using the same image data), thus enabling adaptation of the temperature determination, e.g. the applied TAS algorithm, for various anatomical ROIs. For instance, dedicated calibration parameters may be used for an area around the forehead.

Further, in yet another embodiment, a camera with depth sensing (Time-of-Flight or structured light) can be used to scan the head to acquire the geometric structure of the head. By combining PPG imaging with the facial geometrics, the ROI can be more accurately segmented or tracked for core temperature measurement.

Advantageous applications of the invention may be in the field of continuous or spot-check monitoring in NICU, a baby phone with temperature monitoring, and patient monitoring, but other applications are generally possible as well.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for determining a core body temperature of a subject, said system comprising:
   an imaging unit for acquiring image data of skin of the subject,
   a thermal sensor for acquiring thermal sensor data of the skin of the subject,
   a processor; and
   a non-transitory computer-readable storage medium comprising instructions which, when executed by the processor, cause the apparatus to:
   receive the image data of the skin of the subject;
   receive the thermal sensor data of the skin of the subject;
   derive photoplethysmography (PPG) signals from the image data;
   automatically detect one or more skin areas having strongest PPG signals;
   determine the core body temperature of the subject from the thermal sensor data for the detected one or more skin areas with the strongest PPG signals;
   identify one or more of an anatomical region or a geometrical structure of the subject, with areas of high blood pulsatility and areas of small blood pulsatility, within the obtained image data; and
   adapt the determination of the core body temperature according to the identified one or more of the anatomical region or the geometrical structure of the subject, with the areas of high blood pulsatility and the areas of small blood pulsatility, based on a difference between calibration parameters, comprising a hottest skin spot, for the identified one or more of the anatomical region or the geometrical structure of the subject.

2. The system as claimed in claim 1,
   wherein said thermal sensor comprises a longwave camera unit for acquiring thermal images in a longwave infrared spectrum.

3. The system as claimed in claim 1,
   wherein said imaging unit comprises an imaging unit for acquiring images in one or more of a visible light spectrum or an infrared light spectrum.

4. A method for determining a core body temperature of a subject, said method comprising:
   obtaining image data of skin of the subject,
   acquiring thermal sensor data of the skin of the subject,
   deriving photoplethysmography (PPG) signals from the obtained image data,
   automatically detecting one or more skin areas having strongest PPG signals,
   determining the core body temperature of the subject from the acquired thermal sensor data for the detected one or more skin areas with the strongest PPG signals;
   identifying one or more of an anatomical region or a geometrical structure of the subject, with areas of high blood pulsatility and areas of small blood pulsatility, within the obtained image data; and
   adapting the determined core body temperature according to the identified one or more of the anatomical region or the geometrical structure of the subject, with the areas of high blood pulsatility and the areas of small blood pulsatility, based on a difference between calibration parameters, comprising a hottest skin spot, for the identified one or more of the anatomical region or the geometrical structure of the subject.

5. The method of claim 4, wherein detecting the one or more skin areas having the strongest PPG signals comprises detecting, based on said PPG signals, one or more skin areas having a highest blood pulsatility.

6. The method of claim 4, wherein detecting the one or more skin areas having the strongest PPG signals comprises detecting one or more skin areas having PPG signals with a highest intensity in a predetermined frequency range.

7. The method of claim 4, wherein determining the core body temperature of the subject comprises analyzing a difference between a temperature of a skin area of the one or more skin areas showing a strongest PPG signal with a temperature of other skin areas.

8. An apparatus to determine a core body temperature of a subject, comprising:
   a processor; and
   a non-transitory computer-readable storage medium comprising instructions which, when executed by the processor, cause the apparatus to:
   receive input image data of skin of the subject;
   receive input thermal sensor data of the skin of the subject;
   derive photoplethysmography (PPG) signals from the image data;
   automatically detect one or more skin areas having strongest PPG signals;
   determine the core body temperature of the subject from the thermal sensor data for the detected one or more skin areas with the strongest PPG signals;
   identify one or more of an anatomical region or a geometrical structure of the subject, with areas of high blood pulsatility and areas of small blood pulsatility, within the obtained image data; and
   adapt the determination of the core body temperature according to the identified one or more of the anatomical region or the geometrical structure of the subject, with the areas of high blood pulsatility and the areas of small blood pulsatility, based on a difference between calibration parameters, comprising a hottest skin spot, for the identified one or more of the anatomical region or the geometrical structure of the subject.

9. The apparatus as claimed in claim 8,
   wherein the instructions, when executed, cause the apparatus to detect the one or more skin areas having the strongest PPG signals by detecting, based on said PPG signals, one or more skin areas having a highest blood pulsatility.

10. The apparatus as claimed in claim 8,
    wherein the instructions, when executed, cause the apparatus to detect the one or more skin areas having the strongest PPG signals by detecting one or more skin areas having PPG signals with a highest intensity in a predetermined frequency range.

11. The apparatus as claimed in claim 8,
    wherein the instructions, when executed, cause the apparatus to determine the core body temperature of the subject by analyzing a difference between a temperature of a skin area of the one or more skin areas showing a strongest PPG signal with a temperature of other skin areas.

12. The apparatus as claimed in claim 8,
    wherein the instructions, when executed, cause the apparatus to determine the core body temperature of the subject from the received thermal sensor data separately for two or more detected skin areas and to combine the determined core body temperature values determined for the two or more detected skin areas.

13. The apparatus as claimed in claim 8, wherein the instructions, when executed, cause the apparatus to track the one or more detected skin areas over time.

14. The apparatus of claim 8, wherein the one or more of the anatomical region or the geometrical structure of the subject is identified via an imaging sensor with depth sensing using time-of-flight or structured light.

15. A non-transitory computer-readable storage medium comprising a set of instructions which, when executed by a computing system, cause the computing system to:
receive input image data of skin of a subject;
receive input thermal sensor data of the skin of the subject;
derive photoplethysmography (PPG) signals from the image data;
automatically detect one or more skin areas having strongest PPG signals; and
determine a core body temperature of the subject from the thermal sensor data for the detected one or more skin areas with the strongest PPG signals;
identify one or more of an anatomical region or a geometrical structure of the subject, with areas of high blood pulsatility and areas of small blood pulsatility, within the obtained image data; and
adapt the determination of the core body temperature according to the identified one or more of the anatomical region or the geometrical structure of the subject, with the areas of high blood pulsatility and areas of small blood pulsatility, based on a difference between calibration parameters, comprising a hottest skin spot, for the identified one or more of the anatomical region or the geometrical structure of the subject.

16. The non-transitory computer-readable storage medium of claim 15, wherein the instructions, when executed, cause the computing system to detect the one or more skin areas having the strongest PPG signals by detecting, based on said PPG signals, one or more skin areas having a highest blood pulsatility.

17. The non-transitory computer-readable storage medium of claim 15, wherein the instructions, when executed, cause the computing system to detect the one or more skin areas having the strongest PPG signals by detecting one or more skin areas having PPG signals with a highest intensity in a predetermined frequency range.

18. The non-transitory computer-readable storage medium of claim 15, wherein the instructions, when executed, cause the computing system to determine the core body temperature of the subject by analyzing a difference between a temperature of a skin area of the one or more skin areas showing a strongest PPG signal with a temperature of other skin areas.

* * * * *